US00PP30628P3

(12) United States Plant Patent
Fouillet

(10) Patent No.: US PP30,628 P3
(45) Date of Patent: Jul. 2, 2019

(54) APPLE TREE NAMED 'HC2-1'

(50) Latin Name: *Malus domestica*
Varietal Denomination: HC2-1

(71) Applicant: International Fruit Obtention (IFO) GIE, Seiches sur le Loir (FR)

(72) Inventor: Valérie Fouillet, Saint Sylvain d'Anjou (FR)

(73) Assignee: International Fruit Obtentions (IFO) GIE, Seiches sur le Loir (FR)

( * ) Notice: Subject to any disclaimer, the term of this patent is extended or adjusted under 35 U.S.C. 154(b) by 0 days.

(21) Appl. No.: 15/732,161

(22) Filed: Sep. 26, 2017

(65) Prior Publication Data

US 2018/0098471 P1 Apr. 5, 2018

Related U.S. Application Data

(60) Provisional application No. 62/496,006, filed on Sep. 30, 2016.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05); *A01H 5/08* (2013.01)

(58) Field of Classification Search
USPC ..... Plt./161
CPC ..... A01H 5/0875; A01H 5/08; A01H 5/02; A01H 5/0222; A01H 6/7418
See application file for complete search history.

(56) References Cited

U.S. PATENT DOCUMENTS

PP7,880 P * 6/1992 Cripps ..... Plt./161

* cited by examiner

*Primary Examiner* — June Hwu
(74) *Attorney, Agent, or Firm* — Michelle Bos Legal LLC

(57) ABSTRACT

'HC2-1' apple tree is a new variety selected for its productivity and its attractive early maturing fruit.

7 Drawing Sheets

Latin name: *Malus domestica.*
Variety denomination: 'HC2-1'.

BACKGROUND OF THE VARIETY

'HC2-1' is a new and distinct variety of apple tree (*Malus domestica*) obtained from a controlled cross of female parent 'DL33' and male parent 'HY46-3', carried out at Seiches sur le Loir, France in 2003. Seeds obtained from the cross were planted at Seiches sur le Loir, and 'HC2-1' was selected from the resulting seedlings for propagation and further observation. 'HC2-1' was first asexually propagated by budding in 2009 at Seiches sur le Loir, and has since been observed to remain true to type over successive asexually propagated generations.

BRIEF DESCRIPTION OF THE VARIETY

'HC2-1' apple tree is distinguished by its productivity, and by its attractive early-maturing fruit.

Fruit of 'HC2-1' is distinguished from female parent 'DL33' by its earlier maturity, shiny solid flush overcolor, and finer, crispier flesh, as described in Table 1

TABLE 1

Comparison of 'HC2-1' to 'DL33'

| | 'HC2-1' | 'DL33' |
|---|---|---|
| Harvest maturity | Sep. 5, 2016; Aug. 25, 2017 | Sep. 20, 2016; Sep. 20, 2017 |

TABLE 1-continued

Comparison of 'HC2-1' to 'DL33'

| | 'HC2-1' | 'DL33' |
|---|---|---|
| Luster of skin | Shiny | Dull to slightly shiny |
| Fruit flesh texture | Crisp, fine texture | Slightly crisp, grainy to medium texture |
| Amount of overcolor | Very large area covered, with some visible background color on each fruit | Nearly 100% |

Fruit of 'HC2-1' is distinguished from male parent 'HY46-3' by its orange-red skin color as compared to the yellow skin color of 'HY46-3'. 'HC2-1' is also distinguished by its less greasy skin, more balanced taste, earlier harvest maturity, and smaller size.

Fruit of 'HC2-1' is distinguished from similar variety 'Gala' (U.S. Plant Pat. No. 3,637) by its more pronounced aroma, improved storage ability, larger size, more acidic flesh, and more highly colored skin, as described in Table 2.

TABLE 2

Comparison of 'HC2-1' to 'Gala'

| | 'HC2-1' | 'Gala' |
|---|---|---|
| Fruit aroma | Pronounced | Light |
| Fruit size | Medium to large | Small to medium |
| Fruit flavor | Sweet and acid | Sweet |

TABLE 2-continued

| Comparison of 'HC2-1' to 'Gala' | | |
|---|---|---|
| | 'HC2-1' | 'Gala' |
| Fruit skin color | Bright, intense orange red | Dark red |
| Storageability | 4 to 5 months | 3 to 4 months |

BRIEF DESCRIPTION OF THE PHOTOGRAPHS

The accompanying photographs of the 'HC2-1' variety were taken of five- and six-year-old trees in 2016 and 2017 at Seiches sur le Loir, France.

DETAILED BOTANICAL DESCRIPTION OF THE VARIETY

Figure 1:
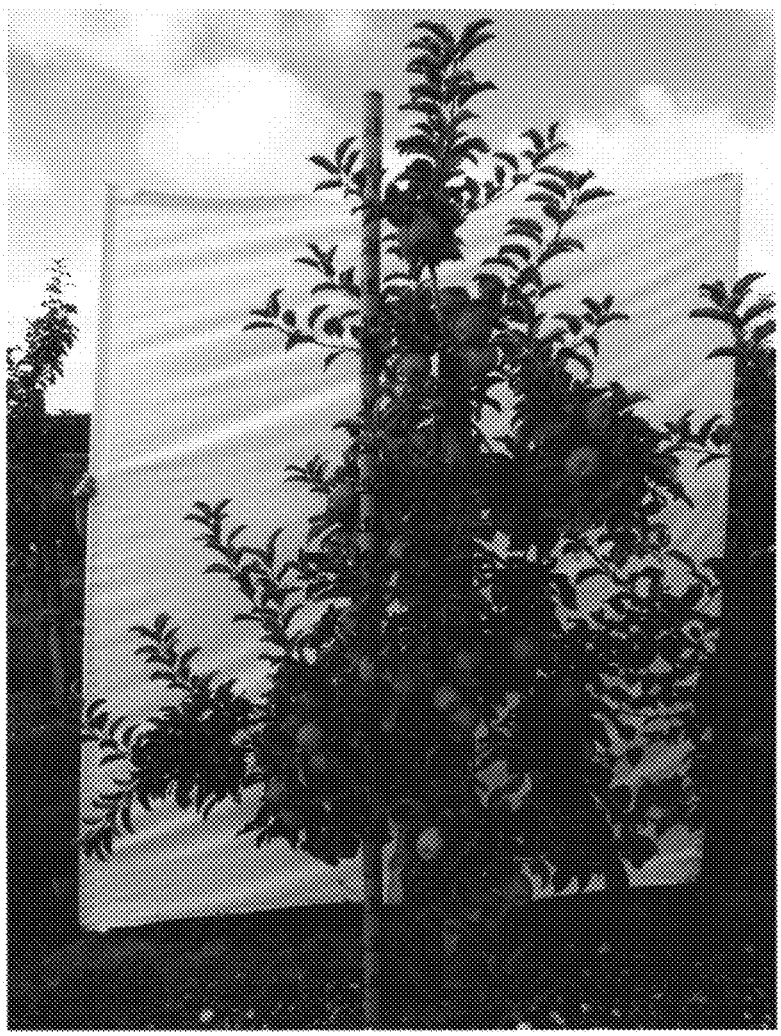
FIG. 1 shows an 'HC2-1' apple tree.
Figure 2:
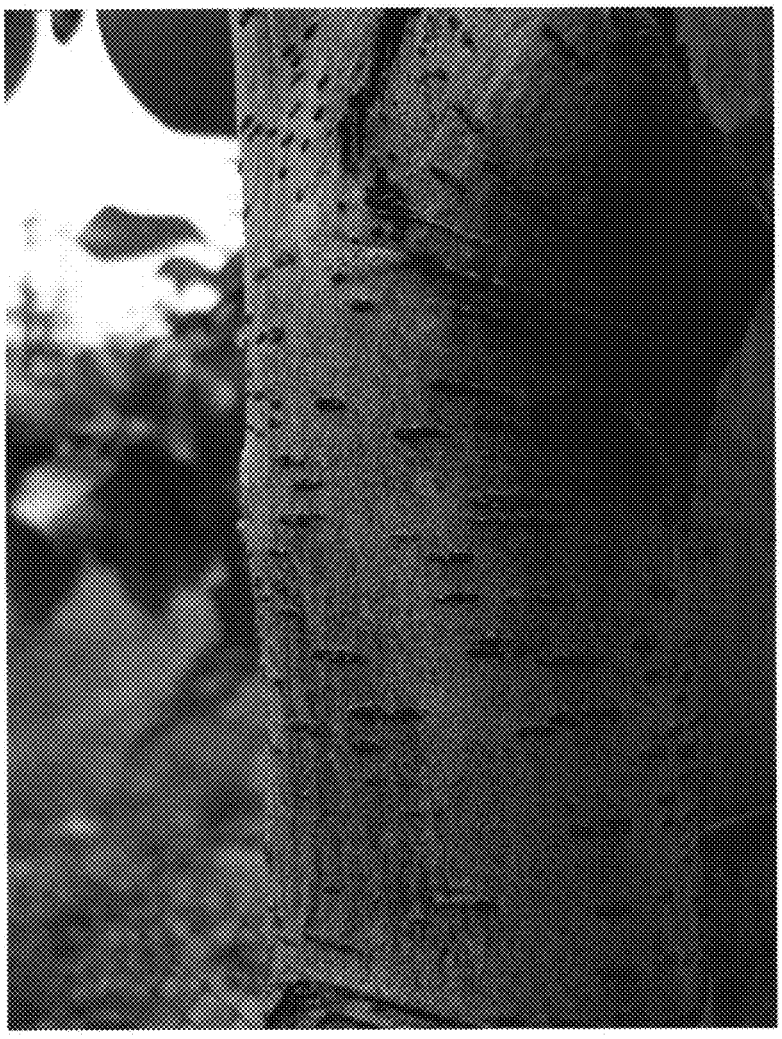
FIG. 2 shows the trunk of an 'HC2-1' apple tree.
Figure 3:
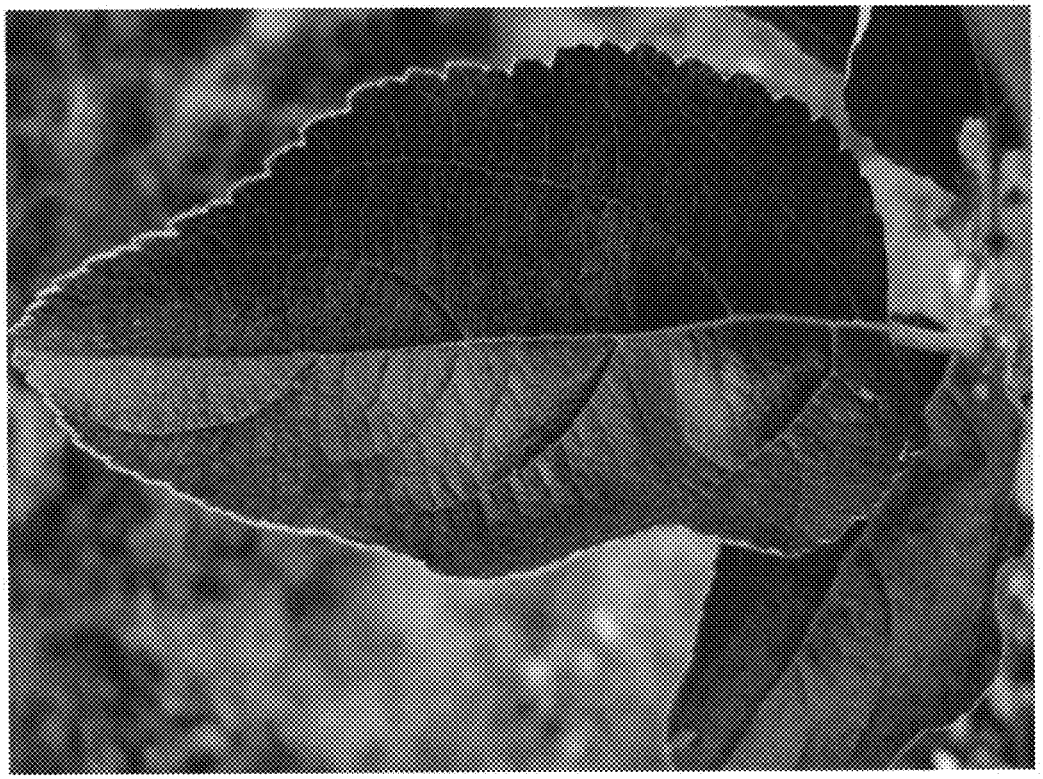
FIG. 3 shows a leaf of an 'HC2-1' apple tree.
Figure 4:
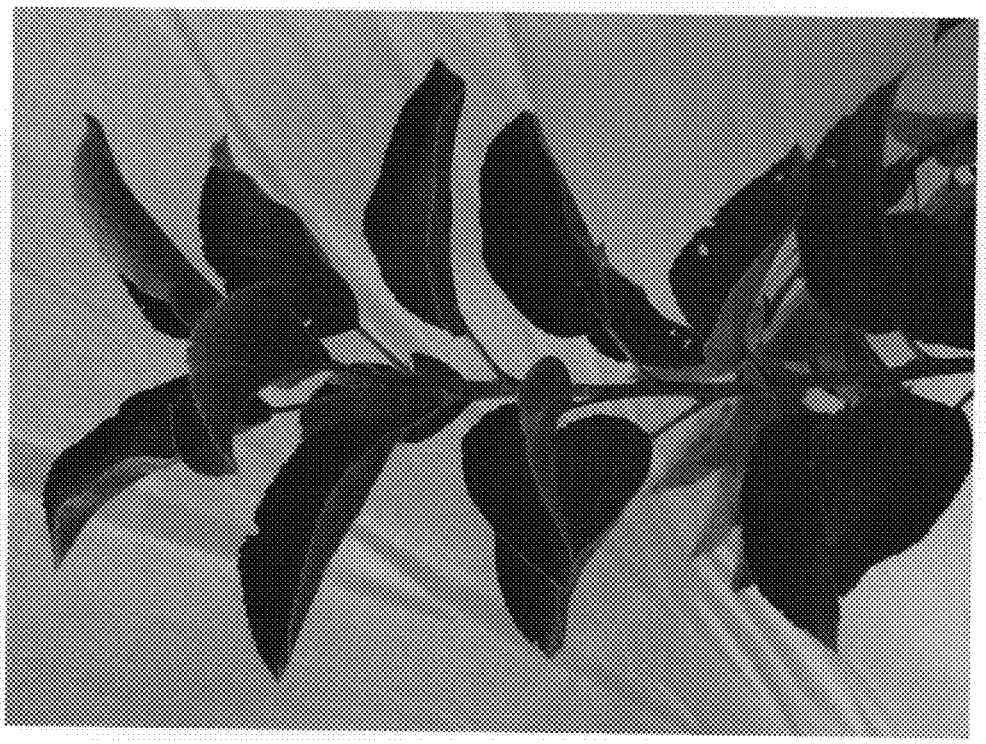
FIG. 4 shows a young shoot and leaves of an 'HC2-1' apple tree.
Figure 5:
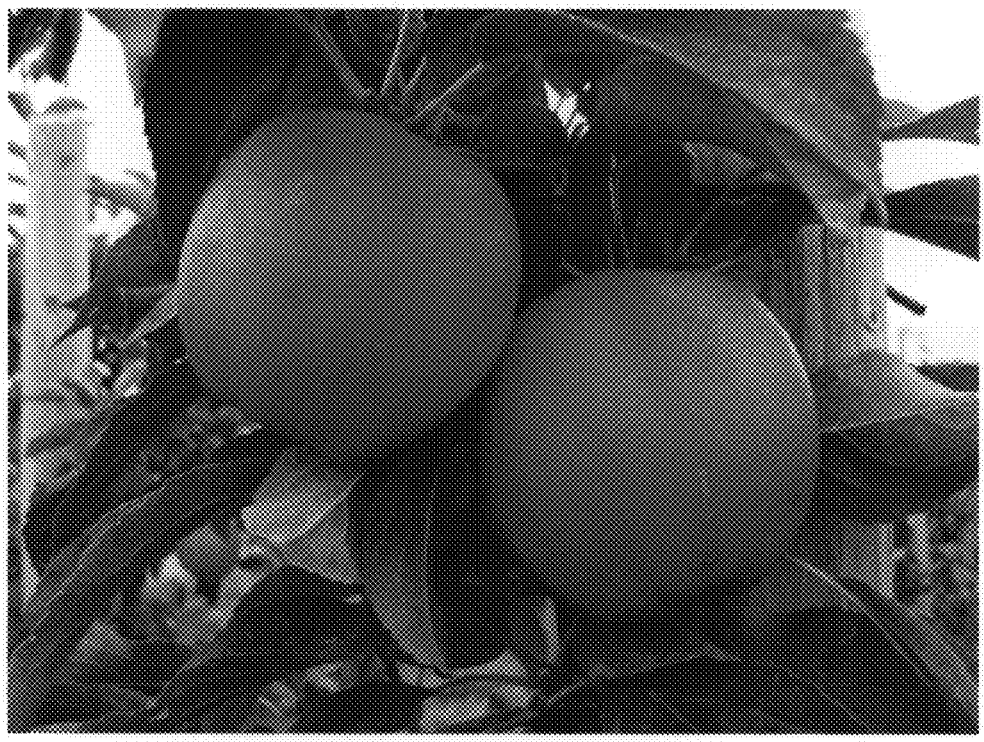
FIGS. 5 and 6 show 'HC2-1' apples.
Figure 6:
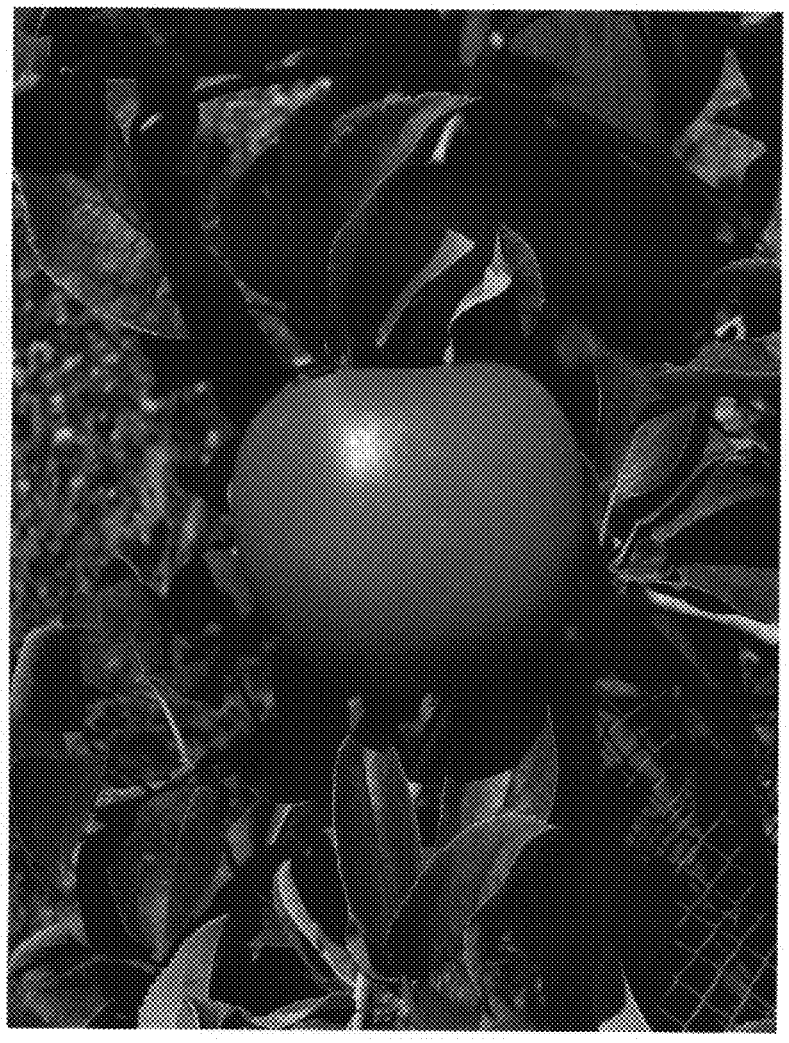
Figure 7:
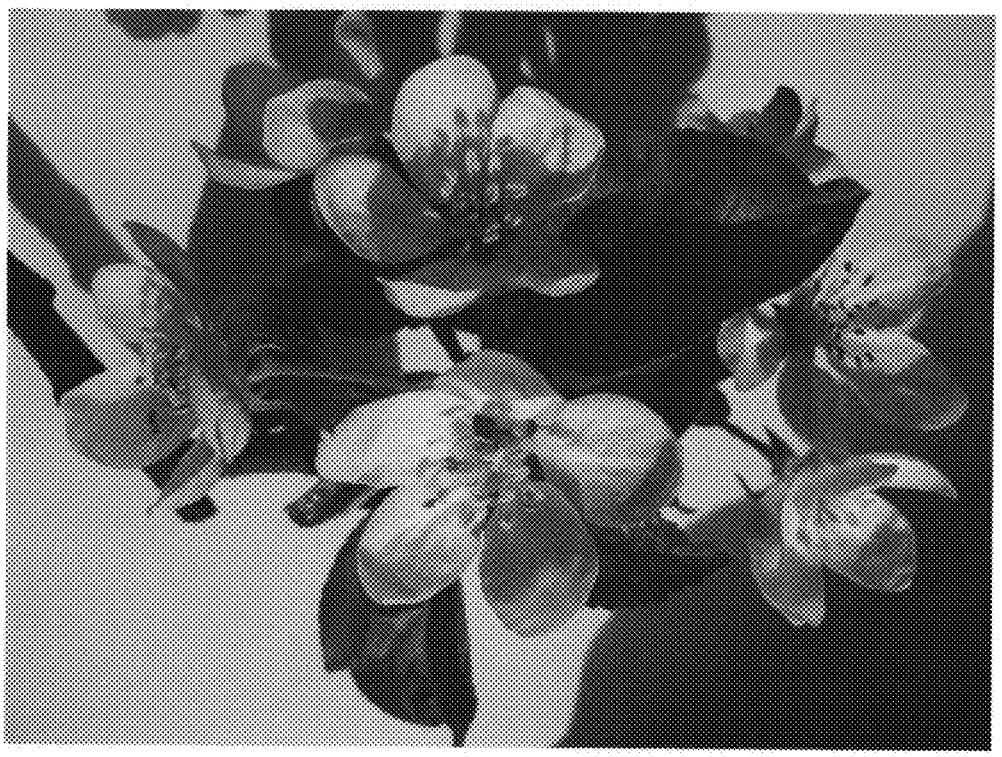
FIG. 7 shows the blossoms of an 'HC2-1' apple tree.

The following detailed botanical description is based on observations made at Seiches sur le Loir, France during the 2016 and 2017 growing seasons, of five- and six-year-old trees grown on Pajam®2 'Cepiland' rootstock (U.S. Plant Pat. No. 7,715). All colors are described according to The Royal Horticultural Society Mini Colour Chart (2005). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium.
*Type*.—Ramified.
*Habit*.—Drooping.
*Height*.—Approximately 2.4 m.
*Trunk diameter* (*at* 30 *cm above the graft*).—52 mm.
*Bark texture*.—Smooth.
*Bark color*.—Grey N200C.
*Bearing*.—On spurs and long shoots.

Branch (fruiting branches located at around 1 m above the graft union):

*Length*.—75 cm.
*Diameter*.—14 mm.
*Crotch angle*.—90°.
*Bark color*.—Grey N200C.
*Lenticel length*.—2.5 mm.
*Lenticel color*.—Dark orange yellow 22A.
*Number of lenticels per cm*$^2$.—5.

One year old shoot:

*Length*.—50 cm.
*Color*.—Dark brown 200B.
*Pubescence*.—Medium to strong.
*Thickness*.—55 mm to 85 mm.
*Internode length*.—25 mm.
*Number of lenticels per cm*$^2$.—10.

Flower buds:

*Quantity per spur*.—1 to 8.
*Shape*.—Conical to rounded.
*Length*.—11 mm.
*Diameter*.—10 mm.
*Color*.—Purple brown 166A.

Flowers:

*Diameter of fully open flower*.—36 mm.
*Relative position of petal margin*.—Mostly overlapping, with some intermediate.
*Number per cluster*.—5.
*Date of first bloom*.—Apr. 3, 2017.
*Date of full bloom*.—Apr. 5, 2017 (2 days before 'Golden Delicious').
*Pollination requirement*.—Pollenizer required ('Granny Smith', 'Braeburn', 'Cripps Pink' (U.S. Plant Pat. No. 7,880), 'Ida red'.

Petals:

*Number per flower*.—5.
*Shape*.—Elliptical.
*Length*.—20 mm.
*Width*.—13 mm.
*Apex*.—Obtuse.
*Base*.—Acute.
*Margin*.—Smooth.
*Color of upper surface*.—White 155B with pink veins 70C.
*Color of lower surface*.—White 155B with pink 70C.

Pistils:

*Size*.—10 mm.
*Color*.—Light yellow green 149A.
*Quantity per flower*.—5.

Stigma:

*Size*.—1 mm.
*Color*.—Light yellow green 149A.
*Position*.—Below anthers.

Style:

*Size*.—9 mm.
*Color*.—Light yellow green 149A.

Ovary:

*Size*.—4 mm.
*Color*.—Brown green 152D.

Anthers:

*Quantity*.—20.
*Size*.—2 mm.
*Presence of pollen*.—Yes.
*Color of pollen*.—Light yellow 8C.

Pedicel:

*Length*.—27 mm.
*Diameter*.—2 mm.
*Color*.—Yellow green 145B.

Sepals:

*Quantity*.—5.
*Coloration*.—Light green 141D.
*Shape*.—Pointed.
*Margin*.—Smooth.

Leaves:

*Shape*.—Elliptical.
*Length*.—93 mm.
*Width*.—51 mm.
*Length/width ratio*.—1.82.
*Blade margin*.—Crenate.
*Apex*.—Acute.
*Base shape*.—Right-angled.
*Color of upper surface*.—Dark green 137A.
*Color of lower surface*.—Green 137C.

*Texture*.—Upper surface — Glabrous.
*Texture*.—Lower surface — Mildly pubescent.
*Attitude in relation to shoot*.—Upwards.

Petiole:
*Length*.—27 mm.
*Diameter*.—1.6 mm.
*Coloration*.—Green 194A and purple brown 181A.

Fruit:
*Quantity per cluster*.—2 to 3.
*Diameter*.—73 mm.
*Height*.—73 mm.
*Weight*.—163 g.
*Ratio of height to width*.—0.87.
*General shape in profile*.—Globose.
*Position of maximum diameter*.—Upper middle of height.
*Ribbing*.—Moderate.
*Crowning at calyx end*.—Strong.
*Size of eye*.—Medium.
*Aperture of eye*.—Closed.
*Length of sepal*.—7 mm.
*Bloom of skin*.—Weak.
*Greasiness of skin*.—Weak.
*Amount of over color*.—Very large.
*Over color of skin*.—Orange red 41B.
*Intensity of over color*.—Medium.
*Pattern of over color*.—Only solid flush.
*Lenticels*.—About 3 per $cm^2$, small to medium size.
*Amount of russet around stalk cavity*.—Medium.
*Amount of russet on cheeks*.—Absent or weak.
*Area of russet around eye basin*.—Absent or weak.
*Length of stalk*.—23 mm.
*Thickness of stalk*.—2.5 mm.
*Depth of stalk cavity*.—13 mm.
*Width of stalk cavity*.—31 mm.
*Depth of eye basin*.—7 mm.
*Width of eye basin*.—27 mm.
*Firmness of flesh*.—Medium.
*Flesh texture*.—Medium to fine.
*Aroma*.—High.
*Juiciness*.—Medium to high.
*Brix*.—13.5 ° Brix.
*Flesh coloration*.—Light Yellow 4D.
*Stem coloration*.—Red Brown 171A and green 139C.

Seeds:
*Quantity per fruit*.—7 to 9.
*Shape*.—Oval-oblong.
*Coloration*.—Purple Brown 166A.

Harvest:
*Time for harvest*.—2 to 3 days after Gala; Sep. 5, 2016 and Aug. 25, 2017 at Maine et Loire, France.
*Number of picks*.—2 to 3.
*Fruit load per tree*.—High; around 23 kg per tree.

Disease resistance/susceptibility: No resistance noted.
Temperature resistance: Good heat and cold resistance in temperate areas.
Fruit shipping quality: Good.
Fruit storage life: 4 to 5 months.
Market use: Fresh eating.

I claim:

1. A new and distinct apple tree substantially as described and illustrated herein.

* * * * *